United States Patent
Bawendi et al.

(10) Patent No.: US 7,125,605 B2
(45) Date of Patent: Oct. 24, 2006

(54) HIGHLY LUMINESCENT COLOR-SELECTIVE NANOCRYSTALLINE MATERIALS

(75) Inventors: Moungi Bawendi, Boston, MA (US); Klavs F. Jensen, Lexington, MA (US); Bashir O. Dabbousi, Dhahran (SA); Javier Rodriguez-Viejo, Sant Cugat del Valles (ES); Frederic Victor Mikulec, Somerville, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 18 days.

(21) Appl. No.: 10/960,947

(22) Filed: Oct. 12, 2004

(65) Prior Publication Data

US 2005/0048283 A1 Mar. 3, 2005

Related U.S. Application Data

(63) Continuation of application No. 10/642,578, filed on Aug. 19, 2003, now Pat. No. 6,861,155, which is a continuation of application No. 09/625,861, filed on Jul. 26, 2000, now Pat. No. 6,607,829, and a continuation-in-part of application No. 08/969,302, filed on Nov. 13, 1997, now Pat. No. 6,322,901.

(60) Provisional application No. 60/145,708, filed on Jul. 26, 1999.

(51) Int. Cl.
  *B32B 5/16* (2006.01)
(52) U.S. Cl. .................. 428/403; 977/813; 977/832
(58) Field of Classification Search .............. 428/402, 428/403
  See application file for complete search history.

(56) References Cited

U.S. PATENT DOCUMENTS

| | | | |
|---|---|---|---|
| 3,996,345 A | 12/1976 | Ullman et al. | 424/12 |
| 4,637,988 A | 1/1987 | Hinshaw et al. | 436/546 |
| 4,777,128 A | 10/1988 | Lippa | 435/5 |
| 5,262,357 A | 11/1993 | Alivisatos et al. | 437/233 |
| 5,293,050 A | 3/1994 | Chapple-Sokol et al. | 257/17 |
| 5,304,786 A | 4/1994 | Pavlidis et al. | 235/462 |
| 5,354,707 A | 10/1994 | Chapple-Sokol et al. | 437/106 |
| 5,395,791 A | 3/1995 | Cheng et al. | |
| 5,422,489 A | 6/1995 | Bhargava | 250/488.1 |
| 5,434,878 A | 7/1995 | Lawandy | |
| 5,492,080 A | 2/1996 | Ohkawa et al. | |
| 5,499,260 A | 3/1996 | Takahashi et al. | |
| 5,505,928 A | 4/1996 | Alivisatos et al. | 423/299 |
| 5,515,393 A | 5/1996 | Okuyama et al. | |
| 5,525,377 A | 6/1996 | Gallagher et al. | 427/512 |
| 5,537,000 A | 7/1996 | Alivisatos et al. | 313/506 |

(Continued)

FOREIGN PATENT DOCUMENTS

WO  WO 95/29473  11/1995

(Continued)

OTHER PUBLICATIONS

Ekimov, A.I., et al., "Quantum Confined Atoms of Doped ZnO Nanocrystals," *Phys. Stat. Sol* (b) 229, No. 2, 897-901 (2002).

(Continued)

*Primary Examiner*—H. Thi Le
(74) *Attorney, Agent, or Firm*—Steptoe & Johnson LLP

(57) ABSTRACT

A nanocrystal capable of light emission includes a nanoparticle having photoluminescence having quantum yields of greater than 30%.

30 Claims, 4 Drawing Sheets

U.S. PATENT DOCUMENTS

| | | | |
|---|---|---|---|
| 5,541,948 | A | 7/1996 | Krupke et al. |
| 5,565,324 | A | 10/1996 | Still et al. .................... 435/6 |
| 5,585,640 | A | 12/1996 | Huston et al. ............ 250/483.1 |
| 5,625,456 | A | 4/1997 | Lawandy .................... 356/376 |
| 5,674,698 | A | 10/1997 | Zarling et al. ............. 435/7.92 |
| 5,711,803 | A | 1/1998 | Pehnt et al. |
| 5,721,099 | A | 2/1998 | Still et al. .................... 435/6 |
| 5,736,330 | A | 4/1998 | Fulton ............................ 435/6 |
| 5,747,180 | A | 5/1998 | Miller et al. |
| 5,751,018 | A | 5/1998 | Alivisatos et al. |
| 5,770,299 | A | 6/1998 | Dannenhauer et al. ....... 428/195 |
| 5,789,162 | A | 8/1998 | Dower et al. .................... 435/6 |
| 5,882,779 | A | 3/1999 | Lawandy |
| 5,985,353 | A | 11/1999 | Lawton et al. ............. 427/2.13 |
| 5,990,479 | A | 11/1999 | Weiss et al. ................. 250/307 |
| 6,207,229 | B1 * | 3/2001 | Bawendi et al. ............ 427/215 |
| 6,306,610 | B1 | 10/2001 | Bawendi et al. |
| 6,322,901 | B1 | 11/2001 | Bawendi et al. |
| 6,423,551 | B1 | 7/2002 | Weiss et al. |
| 6,861,155 | B1 * | 3/2005 | Bawendi et al. ............ 428/549 |
| 2002/0066401 | A1 | 6/2002 | Peng et al. |
| 2003/0017264 | A1 | 1/2003 | Treadway et al. |

FOREIGN PATENT DOCUMENTS

| | | |
|---|---|---|
| WO | WO 97/10175 | 3/1997 |
| WO | WO 98/04740 | 2/1998 |
| WO | 98/19963 | 5/1998 |
| WO | WO 98/33070 | 7/1998 |
| WO | WO 98/36376 | 8/1998 |
| WO | WO 98/46372 | 10/1998 |
| WO | WO 99/26299 | 5/1999 |

OTHER PUBLICATIONS

Ekimov, A.I. et al., "Spin-flip and acoustic-phonon Raman scattering in CdS nanocrystals," *Physical Review B*, vol. 58, No. 4, 15 (Jul. 1998-II), 2077-2087.

Ekimov, A.I. et al., "CdS nanocrystal growth in thin silica films: evolution of size distribution function," *Journal of Crystal Growth* 184/185 (1998) 360-364.

Ekimov, A.I. et al., "Dynamics of excitons in CuBr nanocrystals: Spectral-hole burning and transient four-wave-mixing measurements," *Physical Review B*, vol. 57, No. 3, Jan. 15, 1998-I, 1774-1783.

Ekimov, A.I. et al., "Size-selective resonant Raman scattering in CdS doped glasses," *Physical Review B*, vol. 57, No. 1, Jan. 1, 1998-I, 341-346.

Ekimov, A.I. et al., "Growth and optical properties of semiconductor nanocrystals in a glass matrix," *Journal of Luminescence* 70 (1996) 1-20.

Ekimov, A.I. et al., "Size dependence of acoustic and optical vibrational modes of CdSe nanocrystals in glasses," *Journal of Non-Crystalline Solids* 197 (1996) 238-246.

Ekimov, A.I. et al., "Subpicosecond dynamics of confined excitons in CuCl nanocrystals," *Materials Science and Engineering* A217/218 (1996) 167-170.

Ekimov, A.I. et al., "Enhancement of electron-hole exchange interaction in CdSe nanocrystals; A quantum confinement effect," *Physical Review B*, vol. 53, No. 3, Jan. 15, 1996-I, 1336-1342.

Ekimov, A.I. et al., "Subpicosecond dynamics of confined excitons and optical nonlinearities of CuCl quantum dots," *Journal of Luminescence* 66 & 67 (1996) 406-409.

Ekimov, A.I. et al., "Size-dependent Electron-Hole Exchange Interaction in CdSe Quantum Dots, *Il Nuovo Cimento*," vol. 17, Nos. 11-12, (1995) 1407-1412.

Ekimov, A.I. et al., "Polaron and Exciton-Phonon Complexes in CuCl Nanocrystals," *Physical Review Letters*, vol. 74, No. 9, Feb. 27, 1995, p. 1645.

Ekimov, A.I. et al., "Growth of CdSe nanocrystals in ion-implanted $SiO_2$ films," *Journal of Crystal Growth* 151 (1995) 38-45.

Ekimov, A.I. et al., "Effects of Resonance on Low-Frequency Raman Scattering From Semiconductor Nanocrystals," *Radiation Effects and Defects in Solids*, 1995, vol. 137, pp. 45-50.

Ekimov, A.I. et al., "Optical Properties of Oxide Glasses Doped by Semiconductor Nanocrystals," *Radiation Effects and Defects in Solids*, 1995, vol. 134, pp. 11-22.

Ekimov, A.I. et al., "Enhancement of Exciton Exchange Interaction by Quantum Confinement in CdSe Nanocrystals," *Jpn. J. Appl. Phys*, vol. 34, 12-14 (1994).

Ekimov, A.I. et al., "Growth of CdS nanocrystals in silicate glasses and in thin $SiO_2$ films in the Initial states of the phase separation of a solid solution," *Semiconductors*, 28 (5), May 1994, 486-493.

Ekimov, A.I. et al., "Interface effects on the properties of confined excitons in CuCl microcrystals," *Journal of Luminescence* 60 & 61 (1994) 396-399.

Ekimov, A. I., "Surface Recombination of Nonequilibrium Electron-Hole Plasma in Laser-Modified Semiconductor-Doped Glasses," *Solid State Communications*, vol. 87, No. 6, 577-580 (1993).

Ekimov, A I. "Dynamics of Nonlinear Optical Response of CuBr-Doped Glasses," *Superlattices and Microstructures*, vol. 3, No. 2, 199-202 (1993).

Ekimov, A. I., "Absorption and intensity-dependent photoluminescence measurements on CdSe quantum dots: assignment of the first electronic transitions," *Journal of the Optical Society of America*, vol. 10, Nos. 1-12, 100-107 (1992).

Ekimov, A.I. et al. "Preparation and investigation of $SIO_2$ films activated by CdS semiconductor nanocrystals," *Soviet Physics Semiconductors*, vol. 26, 57-59 (1992).

Ekimov, A.I. et al. "Generation of reflected second harmonic at semiconductor quantum dots," *JETP Letters*, vol. 55, No. 8, 435-439 (1992).

Ekimov, A.I. et al. "Dimensional Effects in Luminescence Spectra of Zero-Dimensional Semiconductor Structures," *Bulletin of the Russian Academy of Sciences*, vol. 56, No. 2, pp. 154-157, Feb. 1992.

Ekimov, A.I. et al., "Fast switching of the transmission of light by glasses activated with CdS microcrystals," *Sov. Phys. Semicond.*, vol. 25 No. 2, 164-166 (1991).

Ekimov, A.I. et al., "Resonance Raman Spectroscopy of Electron-Hole Pairs—Polar Phonon Coupling in Semiconductor Quantum Microcrystals," *Solid State Communications*, vol. 78, No. 10, pp. 853-856, 1991.

Ekimov, A.I. et al., "Optics of Zero Dimensional Semiconductor Systems, *Acta Physica Polonica A*," vol. 79 (1991), No. 1. pp. 5-14.

Ekimov, A.I. et al., "Optical Properties of Semiconductor Quantum Dots in Glass Matrix," *Physica Scripta.* vol. T39, 217-222 (1991).

Ekimov, A.I. et al., "Rapid Processes of Darkening and Bleaching in CdS Doped Glasses," *Superlattices and Microstructures* vol. 10, No. 3, 307-310 (1990).

Ekimov, A.I. et al., "Auger ionization of semiconductor quantum drops in a glass matrix," *Journal of Luminescence* 47 (1990) 113-127 North-Holland.

Ekimov, A.I. et al., "Time-Resolved Luminescence of CdSe Microcrystals," *Solid State Communications*, vol. 74, No. 7, pp. 555-557, 1990.

Ekimov, A.I. et al., "Quantum-Size Stark Effect in Semiconductor Microcrystals," *Journal of Luminescence* 46 (1990) 97-100 North-Holland.

Ekimov, A.I. et al., "Spectra and Decay Kinetics of Radiative Recombination in CdS Microcrystals," *Journal of Luminescence* 46 (1990) 83-95 North-Holland.

Ekimov, A.I. et al., "Influence of high hydrostatic pressures on the exciton spectrum of CdS microcrystals in glass," *Sov. Phys. Semicond.* 23(9), Sep. 1989, pp. 965-966.

Ekimov, A.I. et al., "Photoluminescence of quasizero-dimensional semiconductor structures," *Sov. Phys. Solid State* 31(8), Aug. 1989, pp. 1385-1393.

Ekimov, A.I. et al., "Photoionization of semiconducting microcrystals in glass," *Sov. Phys. Solid State* 31(1), Jan. 1989, pp. 149-151.

Ekimov, A.I. et al., "Donor-like Exciton in Zero-Dimension Semiconductor Structures," *Solid State Communications*, vol. 69, No. 5, pp. 565-568, 1989.

Ekimov, A.I. et al., "Nonlinear Optics of Semiconductor-Doped Glasses," *Phys. Stat. Sol.* (b) 150, (1988) pp. 627-633.

Ekimov, A.I. et al., "Nonlinear optical properties of semiconductor microcrystals," *JETP Lett.*, vol. 46, No. 10, Nov. 25, 1987 pp. 435-439.

Ekimov, A.I. et al., "Quantization of the energy spectrum of holes in the adiabatic potential of the electron," *JETP Lett.*, vol. 43, No. 6, Mar. 25, 1986, pp. 376-379.

Ekimov, A.I. et al., "Quantum Size Effect in Semiconductor Microcrystals," *Solid State Communications*, vol. 56, No. 11, pp. 921-924, 1985.

Ekimov, A.I. et al., "Size quantization of the electron energy spectrum in a microscopic semiconductor crystal," *JETP Lett.*, vol. 40, No. 8, Oct. 25, 1984, pp. 1136-1139.

Ekimov, A.I. et al., "Quantum size effect in the optical spectra of semiconductor microcrystals," *Sov. Phys. Semicond.* 16(7), Jul. 1982, pp. 775-778.

Ekimov, A.I. et al., "Quantum size effect in three-dimensional microscopic semiconductor crystals," *JETP Lett*, vol. 34, No. 6, Sep. 20, 1981, pp. 345-349.

Ekimov, A.I. et al., "Oscillations of polarization of recombination radiation of a variable gap semiconductor in a magnetic field," *JETP Lett.*, vol. 25 No. 55, 526-528 (1977).

Loher et al., "Epitaxy films of the 3D semiconductor CdS on the 2D layered substrate MX2 prepared by Van der Waals epitaxy" Journal of Crystal Growth, vol. 146, 1995, pp. 408-412.

Tsuji et al., "Characterization of CdS thin film in high efficient CdS/CdTe solar cells", Journal of Crystal Growth, vol. 214/215, 2000, pp. 1142-1147.

Alivisatos, "Semiconductor Clusters, Nanocrystals, and Quantum Dots," *Science*, 271:933-937, Feb. 16, 1996.

Alivisatos et al., "Organization of 'nanocrystal molecules' using DNA", *Nature*, 382:609-611, Aug. 15, 1996.

Baldwin et al., "Synthesis of a Small Molecule Combinatorial Library Encoded with Molecular Tags," *J. Am. Chem. Soc.*, 117:5588-5589, 1995.

Bawendi et al., "Luminescence properties of CdSe quantum crystallites: resonance between interior and surface localized states," *J. Chem. Phys.*, 96(2):946-954, Jan. 15, 1992.

Beverloo et al., "Preparation and Microscopic Visualization of Multicolor Luminescent Immunophosphors," *Cytometry*, 13:561-570, 1992.

Chee et al., "Accessing Genetic Information with High-Density DNA Arrays" *Science*, 274(5287):610-614, Oct. 25, 1996.

Coffer et al., "Characterization of quantum-confined CdS Nanocrystallites stabilized by deoxyribonucleic acid (DNA)" *Nanotechnology*, 3:69-76, 1992.

Colvin et al., "Light-emitting diodes made from cadmium selenide nanocrystals and a semiconducting polymer" *Nature*, 370(6488):354-357, Aug. 4, 1994.

Cook, "Scintillation proximity assay: a versatile high-throughput screening technology," *Drug Discovery Today*, 1(7):287-294, Jul. 1996.

Czarnik, "Encoding methods for combinatorial chemistry" *Curr Opin Chem Biol.*, 1(1):60-66, 1997.

Danek et al., "Synthesis of Luminescent Thin-Film CdSe/ZnSe Quantum Dot Composites Using CdSe Quantum Dots Passivated with an Overlayer of ZnSe" *Chem. Mater.*,8(1):173-180, 1996.

Egner et al., "Tagging in combinatorial chemistry: the use of coloured and fluorescent bads" *Chem. Commun.*, 735-736, Apr. 21, 1997.

Fodor, "Techwire" *Science*, 277(5324):393-395, Jul. 18, 1997.

Guha et al., "Hybrid organic-inorganic semiconductor-based light-emitting diodes" *J. Appl. Phys.*, 82(8):4126-4128, Oct. 15, 1997.

Jarvis et al., "Solution Synthesis and Photoluminescence Studies of Small Crystallites of Cadmium Telluride," *Mat. Res. Soc. Symp. Proc.*, 272:229-234, 1992.

Kagan et al., "Electronic Energy Transfer in CdSe Quantum Dot Solids," *Physical Review Letters*, 76(9):1517-1520, Feb. 26, 1996.

Kagan et al., "Long-range resonance transfer of electronic excitations in close-packed CdSe quantum-dot solids," *Physical Review B*, 54(12):8633-8643, Sep. 15, 1996-II.

Lee et al., "Surface Derivatization of Nanocrystalline CdSe Semiconductors," *Mat. Res. Soc. Symp. Proc.*, 452:323-328, Mar. 13, 1997.

Liz-Marzan et al., "Synthesis of Nanosized Gold-Silica Core-Shell Particles" *Langmuir*, 12(18):4329-4335, 1996.

Mahtab et al., "Protein-Sized Quantum Dot Luminescence Can Distinguish between 'Straight', 'Bent', and 'Kinked' Oligonucletides", *J. Am. Chem. Soc.*, 117:9099-9100, 1995.

Mahtab et al., "Preferential-Absorption of a 'Kinked' DNA to a Neutral Curved Surface: Comparison to and Implications for Non-specific DNA-Pprotein Interactions," *J. Am. Chem. Soc.*, 118(30):7028-7032, 1996.

McGall et al., "Light-directed synthesis of high-density oligonucleotide arrays using semiconductor photoresists" *Proc. Natl. Acad. Sci. USA*, 93:13555-13560, Nov. 1996.

Moran et al., "Radio Frequency Tag Encoded Combinatorial Library Method for the Discovery of Tripeptide-Substituted Cinnamic Acid Inhibitors of the Protein Tyrosine Phosphatase PTP1B" *J. Am. Chem. Soc.*, 117:10787-10788, 1995.

Müllenborn et al., "Characterization of Solution-Synthesized CdTe and HgTe," *Applied Physics*, 56:317-321, 1993.

Murphy et al., "Quantum Dots as Inorganic DNA-Binding Proteins," *Mat. Res. Soc. Symp.*, 452:597-600, Mar. 13, 1997.

Nicolaou et al., "Radiofrequency Encoded Combinatorial Chemistry" *Ingew. Chem. Int. Ed. Engl.*, 34(20):2289-2291, 1995.

Pehnt et al., "Nanoparticle precursor route to low-temperature spray deposition of CdTe thin films," *Appl. Phys. Lett.*, 67(15):2176-2178, Oct. 1995.

Peng et al., "Epitaxial Growth of Highly Luminescent CdSe/CdS Core/Shell Nanocrystals with Photostability and Electronic Accessibility," *J. Am. Chem. Soc.*, 119(30):7019-7029, 1997.

Peng et al., "Synthesis and Isolation of a Homodimer of Cadmium Selenide Nanocrystals," *Angew. Chem. Int. Ed. Engl.*, 36(112):145-147, 1997.

Plunkett et al., "Combinatorial Chemistry and New Drugs" *Sci Am.*, 276(4):68-73, Apr. 1997.

Rogach et al., "Synthesis and Characterization of Thiol-Stabilized CdTe Nanocrystals" *Ber. Bunsenges. Phys. Chem.*, 100(11):1772-1778, Nov. 1996.

Schröck et al., "Multicolor Spectral Karyotyping of Human Chromosomes," *Science*, 273:494-497, Jul. 26, 1996.

Spanhel et al., "Photochemistry of Colloidal Semiconductors. Surface Modification and Stability of Strong Luminescing CdS Particles" *J. Am. Chem. Soc.*, 109(19):5649-5655, 1987.

Steigerwald et al., "Surface Derivatization and Isolation of Semiconductor Cluster Molecules," *J. Am. Chem. Soc.*, 110:3046-3050, 1988.

Whitesell et al., "Directionally Aligned Helical Peptides on Surfaces" *Science*, 261:73-76, Jul. 2, 1993.

"Strongly Photoluminescent CdTe Nanocrystals by Proper Surface Modification," M. Gao et al., *J. Phys. Chem. B.* 102:8360-8363 (1998).

"Photochemistry and Radiation Chemistry of Colloidal Semiconductors. 33. Chemical Changes and Fluorescence in CdTe and ZnTe," U. Resch et al., *Langmuir* 5:1015-1020 (1989).

"An EXAFS Study on Thiolcapped CdTe Nanocrystals," J. Rockenberger et al., *Ber. Bunsenges. Phys. Chem.* 102:1561-1564 (1998).

"Synthesis, Morphology and Optical Properties of Thiol-Stabilized CdTe Nanoclusters in Aqueous Solution," A. L. Rogach et al., *Ber. Bunsenges. Phys. Chem.* 101:1668-1670 (1997).

"Micro photoluminescence spectra of CdTe and CdMnTe self-organized quantum dots," T. Kuroda et al., *Journal of Luminescence* 83-84:321-342 (1999).

"Quantum confinement effects on the optical phonons of CdTe quantum dots," A.M. De Paula et al., *Superlattices and Microstructures* 23:1103-1106 (1998).

"Probing of the quantum dot size distribution in CdTe-doped glasses by photoluminescence excitation spectroscopy," C.R.M. de Oliveira et al., *Appl. Phys. Lett.* 66:439-441 (1995).

"Synthesis and Characterization of Thiol-Stabilized CdTe Nanocrystals," A.L. Rogach et al., *Ber. Bunsenges. Phys. Chem.* 100:1772-1778 (1996).

"Synthesis and Characterization of Surface-Modified Colloidal CdTe Quantum Dots," T. Rajh et al., *J. Phys. Chem.* 97:11999-12003 (1993).

"Nanoparticle precursor route to low-temperature spray deposition of CdTe thin films," M. Pehnt et al., *Appl. Phys. Lett.* 67:2176-2178 (1995).

"Characterization of Solution-Synthesized CdTe and HgTe," M. Müllenborn et al., *Applied Physics* A56:317-321 (1993).

"Solution Synthesis and Photoluminenscence Studies of Small Crystallites of Cadmium Telluride," R. F. Jarvis, Jr. et al., *Mat. Res. Soc. Symp. Proc.*, 272:229-235 (1992).

C.B. Murray et al.; "Synthesis and Characterization of Nearly Monodisperse CdE (E=S,Se,Te) Semiconductor Nanocrystallites"; .*J. Am. Chem. Soc 115*; pp. 8709-8715 (1993).

Database Crossfire Online!; Beilstein Institut zur Forderung der Chemischen Wissenschaft; Beilstein Registry Nos. 2097823 and 1860016; XP002152687—Abstract.

International Search Report (partial) dated Nov. 30, 2000.

Rajh, et al., "Synthesis and Characterization of Surface-Modified Colloidal CdTe Quantum Dots," *J. Phys. Chem.* 97:11999-12003, Nov. 1993.

Lawless, et al., "Bifunctional Capping of CdS Nanoparticles and Bridging to TiO2," *J. Phys. Chem.* 99:10329-10335, 1995.

Gan, et al., "Enhanced Photoluminescence and Characterization of Mn-Doped ZnS Nanocrystallites Synthesized in Microemulsion," *Langmuir* 1997(13):6427-6431, 1997.

Kuno, et al., "The band edge luminescence of surface modified CdSe nanocrystallites: Probing the luminescing state," *J. Chem. Phys.* 106(23):9869-9882, Jun. 1997.

Mikulec, et al., "Synthesis and Characterization of Highly Luminescent (CdSe)ZnS Quantum Dots," *Materials Research Society Symposium*:359-364, Boston, MA, Dec. 2-6, 1997.

Masumoto et al. "Preparation of Monodisperse CdS Nanocrystals by Size Selective Photocorrosion" *J. Phys. Chem.* 100(32):13782 (Aug. 1996).

Colvin et al. "Light-Emitting Diodes Made from Cadmium Selenide Nanocrystals and a Semiconducting Polymer" *Nature* 370:354 (Aug. 1994).

B.O. Dabbousi and M.G. Bawendi "Electroluminescence from CdSe Quantum-Dot/Polymer Composites" *Appl. Phys. Lett.* 66(11):1316 (Mar. 1995).

Kortan et al. "Nucleation and Growth of CdSe on ZnS Quantum Crystallite Seeds, and Vice Versa, in Inverse Micelle Media" *J. Am. Chem. Soc.* 112:1327 (1990).

Nirmal et al. "Fluorescence Intermittency in single Cadmium Selenide Nanocrystals" *Nature* 383:802 (Oct. 1996).

Murray et al. "Synthesis and Characterization of Nearly Monodisperse CdE (E—S, Se, Te) Semiconductor Nanocrystallites" *J. Am. Chem. Soc.* 115:8706 (1993).

Empedocles et al. "Photoluminescence Spectroscopy of Single CdSe Nanocrystallite Quantum Dots" *Phys. Rev. Lett.* 77(18):3873 (Oct. 1996).

M.A. Hines and P. Guyot-Sionnest "Synthesis and Characterization of Strongly Luminescing ZnS-Capped CdSe Nanocrystals" *J. Phys. Chem.* 100:468 (Jan. 1996).

A.P. Alivisatos "Perspectives on the Physical Chemistry of Semiconductor Nanocrystals" *J. Phys. Chem.* 100:13226 (Aug. 1996).

Danek et al. "Synthesis of Luminescent Thin-Film CdSe/ZnSe Quantum Dot Composites Using CdSe Quantum Dots Passivated with an Overlayer of ZnSe" *Materials* 8(1):173 (Jan. 1996).

* cited by examiner

HIGHLY LUMINESCENT COLOR-SELECTIVE NANOCRYSTALLINE MATERIALS

CLAIM OF PRIORITY

This application is a continuation of U.S. patent application Ser. No. 10/642,578, filed on Aug. 19, 2003, which is a continuation of U.S. patent application Ser. No. 09/625,861, filed on Jul. 26, 2000, which claims priority to U.S. Patent Application Ser. No. 60/145,708, filed on Jul. 26, 1999, and is a continuation-in-part of U.S. patent application Ser. No. 08/969,302, filed Nov. 13, 1997, now U.S. Pat. No. 6,322,901, each of which is hereby incorporated by reference.

FEDERALLY SPONSORED RESEARCH OR DEVELOPMENT

This invention was made with government support under Contract No. DMR-94-00334 from the National Science Foundation. The government has certain rights in the invention.

FIELD OF THE INVENTION

This invention relates to luminescent nanocrystalline materials which emit visible light over a very narrow range of wavelengths. The invention further relates to materials which emit visible light over a narrow range tunable over the entire visible spectrum.

BACKGROUND OF THE INVENTION

Semiconductor nanocrystallites (quantum dots) whose radii are smaller than the bulk exciton Bohr radius constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of quantum dots shift to the blue (higher energies) as the size of the dots gets smaller.

Bawendi and co-workers have described a method of preparing monodisperse semiconductor nanocrystallites by pyrolysis of organometallic reagents injected into a hot coordinating solvent (J. Am. Chem. Soc., 115:8706 (1993)). This permits temporally discrete nucleation and results in the controlled growth of macroscopic quantities of nanocrystallites. Size selective precipitation of the crystallites from the growth solution provides crystallites with narrow size distributions. The narrow size distribution of the quantum dots allows the possibility of light emission in very narrow spectral widths.

Although semiconductor nanocrystallites prepared as described by Bawendi and co-workers exhibit near monodispersity, and hence, high color selectivity, the luminescence properties of the crystallites are poor. Such crystallites exhibit low photoluminescent yield, that is, the light emitted upon irradiation is of low intensity. This is due to energy levels at the surface of the crystallite which lie within the energetically forbidden gap of the bulk interior. These surface energy states act as traps for electrons and holes which degrade the luminescence properties of the material.

In an effort to improve photoluminescent yield of the quantum dots, the nanocrystallite surface has been passivated by reaction of the surface atoms of the quantum dots with organic passivating ligands, so as to eliminate forbidden energy levels. Such passivation produces an atomically abrupt increase in the chemical potential at the interface of the semiconductor and passivating layer (See, A. P. Alivisatos, J. Phys. Chem. 100:13226 (1996)). Bawendi et al. (J. Am. Chem. Soc., 115:8706 (1993)) describe CdSe nanocrystallites capped with organic moieties such as tri-n-octyl phosphine (TOP) and tri-n-octyl phosphine oxide (TOPO) with quantum yields of around 5–10%.

Passivation of quantum dots using inorganic materials also has been reported. Particles passivated with an inorganic coating are more robust than organically passivated dots and have greater tolerance to processing conditions necessary for their incorporation into devices. Previously reported inorganically passivated quantum dot structures include CdS-capped CdSe and CdSe-capped CdS (Tian et al., J. Phys. Chem. 100:8927 (1996)); ZnS grown on CdS (Youn et al., J. Phys. Chem. 92:6320 (1988)); ZnS on CdSe and the inverse structure (Kortan et al., J. Am. Chem. Soc. 112:1327 (1990)); and $SiO_2$ on Si (Wilson et al., Science 262:1242 (1993)). These reported quantum dots exhibit very low quantum efficiency and hence are not commercially useful in light emitting applications.

M. A. Hines and P. Guyot-Sionnest report the preparation of ZnS-capped CdSe nanocrystallites which exhibited a significant improvement in luminescence yields of up to 50% quantum yield at room temperature (J. Phys. Chem. 100:468 (1996)). However, the quality of the emitted light remained unacceptable because of the large size distribution (12–15% rms) of the core of the resulting capped nanocrystallites. The large size distribution resulted in light emission over a wide spectral range. In addition, the reported preparation method does not allow control of the particle size obtained from the process and hence does not allow control of color.

Danek et al. report the electronic and chemical passivation of CdSe nanocrystals with a ZnSe overlayer (Chem. Materials 8:173 (1996)). Although it might be expected that such ZnSe-capped CdSe nanocrystallites would exhibit as good as or better quantum yield than the ZnS analogue due to the better unit cell matching of ZnSe, in fact, the resulting material showed only disappointing improvements in quantum efficiency ($\leq 0.4\%$ quantum yield).

Thus there remains a need for semiconductor nanocrystallites capable of light emission with high quantum efficiencies throughout the visible spectrum, which possess a narrow particle size (and hence with narrow photoluminescence spectral range).

It is the object of the invention to provide semiconductor nanocrystallites which overcome the limitations of the prior art and which exhibit high quantum yields with photoluminescence emissions of high spectral purity.

SUMMARY OF THE INVENTION

In one aspect of the invention, a coated nanocrystal capable of light emission includes a substantially monodisperse core selected from the group consisting of CdX, where X=S, Se, Te; and an overcoating of ZnY, where Y=S, Se, and mixtures thereof uniformly deposited thereon, said coated core characterized in that when irradiated the particles emit light in a narrow spectral range of no greater than about 40 nm at full width half max (FWHM). In some embodiments, the narrow spectral range is selected from the spectrum in the range of about 470 nm to about 620 nm and the particle size of the core is selected from the range of about 20 Å to about 125 Å.

In other embodiments of the invention, the coated nanocrystal is characterized in that the nanocrystal exhibits less than a 10% and preferably less than 5%, rms deviation in diameter of the core. The nanocrystal preferably exhibits photoluminescence having quantum yields of greater than 30%, and most preferably in the range of about 30 to 50%.

In another embodiment of the invention, the overcoating comprises one to two monolayers of ZnY. The nanocrystal may further comprise an organic layer on the nanocrystal outer surface. The organic layer may be comprised of moieties selected to provide compatibility with a suspension medium, such as a short-chain polymer terminating in a moiety having affinity for a suspending medium, and moieties which demonstrate an affinity to the quantum dot surface. The affinity for the nanocrystal surface promotes coordination of the organic compound to the quantum dot outer surface and the moiety with affinity for the suspension medium stabilizes the quantum dot suspension.

In another aspect of the invention, a method of preparing a coated nanocrystal capable of light emission includes introducing a substantially monodisperse first semiconductor nanocrystal and a precursor capable of thermal conversion into a second semiconductor material into a coordinating solvent. The coordinating solvent is maintained at a temperature sufficient to convert the precursor into the second semiconductor material yet insufficient to substantially alter the monodispersity of the first semiconducting nanocrystal and the second semiconductor material has a band gap greater than the first semiconducting nanocrystal. An overcoating of the second semiconductor material is formed on the first semiconducting nanocrystal.

In one embodiment of the invention, the monodispersity of the nanocrystal is monitored during conversion of the precursor and overcoating of the first semiconductor nanocrystal. In another embodiment, an organic overcoating is present on the outer nanocrystal surface, obtained by exposing the nanocrystal to an organic compound having affinity for the nanocrystal surface, whereby the organic compound displaces the coordinating solvent.

In addition to having higher quantum efficiencies, ZnS overcoated particles are more robust than organically passivated nanocrystallites and are potentially more useful for optoelectronic devices. The (CdSe)ZnS dots of the invention may be incorporated into electroluminescent devices (LEDs). In addition, the (CdSe)ZnS dots of the invention may exhibit cathodoluminescence upon excitation with both high and low voltage electrons and may be potentially useful in the production of alternating current thin film electroluminescent devices (ACTFELD). In the naming convention used herein to refer to capped nanocrystallites, the compound found within parentheses represents the core compound (i.e. the bare "dot"), while the compound which follows represents the overcoated passivation layer.

These and other features and advantages of the invention are set forth in the description of the invention, which follows.

DETAILED DESCRIPTION OF THE INVENTION

Figure 1:
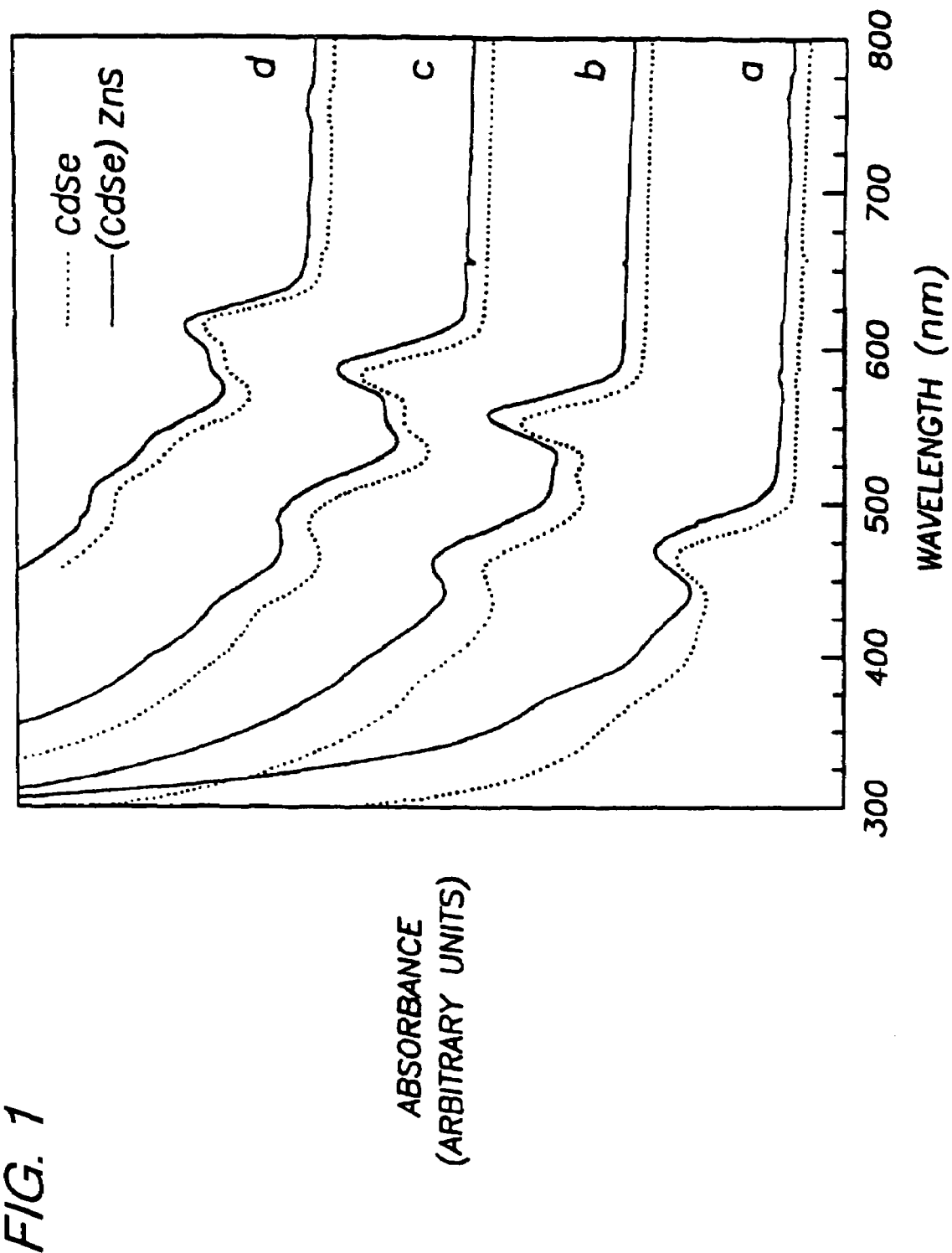
FIG. 1 shows the absorption spectra of CdSe dots with diameters measuring (a) 23 Å, (b) 42 Å, (c) 48 Å and (d) 55 Å before (dashed lines) and after (solid lines) overcoating with 1–2 monolayers of ZnS

The present invention is directed to the preparation of a series of room temperature, highly luminescent ZnS-capped CdSe ((CdSe)ZnS) nanocrystallites having a narrow particle size distribution. Nanocrystallites of the present invention exhibit high quantum yields greater than about 30% and preferably in the range of about 30–50% and a narrow band edge luminescence spanning most of the visible spectrum from 470 nm to 625 nm. The core of the nanocrystallites is substantially monodisperse. By monodisperse, as that term is used herein, it is meant a colloidal system in which the suspended particles have substantially identical size and shape. For the purposes of the present invention, monodisperse particles deviate less than 10% in rms diameter in the core, and preferably less than 5% in the core.

When capped quantum dots of the invention are illuminated with a primary light source, a secondary emission of light occurs of a frequency that corresponds to the band gap of the semiconductor material used in the quantum dot. As previously discussed, the band gap is a function of the size of the nanocrystallite. As a result of the narrow size distribution of the capped nanocrystallites of the invention, the illuminated quantum dots emit light of a narrow spectral range resulting in high purity light. Spectral emissions in a narrow range of no greater than about 60 nm, preferably 40 nm and most preferably 30 nm at full width half max (FWHM) are observed.

The present invention also is directed to a method of making capped quantum dots with a narrow particle size distribution. The capped quantum dots of the invention may be produced using a two step synthesis in which a size selected nanocrystallite is first synthesized and then overcoated with a passivation layer of a preselected thickness. In preferred embodiments, processing parameters such as reaction temperature, extent of monodispersity and layer thickness may be monitored during crystal growth and overcoating to provide a coated quantum dot of narrow particle size distribution, high spectral purity and high quantum efficiency. "Quantum yield" as that term is used herein, means the ratio of photons emitted to that absorbed, e.g., the photoluminescence quantum yield.

The method is described for a (CdSe)ZnS quantum dot, but it is understood that the method may be applied in the preparation of a variety of known semiconductor materials. The first step of a two step procedure for the synthesis of (CdSe)ZnS quantum dots involves the preparation of nearly monodisperse CdSe nanocrystallites. The particles range in size from about 23 Å to about 55 Å with a particle size distribution of about 5–10%. These dots are referred to as "bare" dots. The CdSe dots are obtained using a high temperature colloidal growth process, followed by size selective precipitation.

The high temperature colloidal growth process is accomplished by rapid injection of the appropriate organometallic precursor into a hot coordinating solvent to produce a temporally discrete homogeneous nucleation. Temporally discrete nucleation is attained by a rapid increase in the reagent concentration upon injection, resulting in an abrupt supersaturation which is relieved by the formation of nuclei and followed by growth on the initially formed nuclei. Slow growth and annealing in the coordinating solvent results in uniform surface derivatization and regularity in the core structure.

Injection of reagents into the hot reaction solvent results in a short burst of homogeneous nucleation. The depletion of reagents through nucleation and the sudden temperature drop associated with the introduction of room temperature reagents prevents further nucleation. The solution then may be gently heated to reestablish the solution temperature. Gentle reheating allows for growth and annealing of the crystallites. The higher surface free energy of the small crystallites makes them less stable with respect to dissolution in the solvent than larger crystallites. The net result of this stability gradient is the slow diffusion of material from small particles to the surface of large particles ("Ostwald ripening"). Growth of this kind results in a highly monodisperse colloidal suspension from systems which may initially be highly polydisperse.

Both the average size and the size distribution of the crystallites in a sample are dependent on the growth temperature. The growth temperature necessary to maintain steady growth increases with increasing average crystal size. As the size distribution sharpens, the temperature may be raised to maintain steady growth. As the size distribution sharpens, the temperature may be raised in 5–10° C. increments to maintain steady growth. Conversely, if the size distribution begins to spread, the temperature may be decreased 5–10° C. to encourage Ostwald ripening and uniform crystal growth. Generally, nanocrystallites 40 Angstroms in diameter can be grown in 2–4 hours in a temperature range of 250–280° C. Larger samples (60 Angstroms or more) can take days to grow and require temperatures as high as 320° C. The growth period may be shortened significantly (e.g., to hours) by using a higher temperature or by adding additional precursor materials.

Size distribution during the growth stage of the reaction may be approximated by monitoring the absorption line widths of the particles. Modification of the reaction temperature in response to changes in the absorption spectrum of the particles allows the maintenance of a sharp particle size distribution during growth. It is also contemplated that reactants could be added to the nucleation solution during crystal growth to grow larger crystals.

The particle size distribution maybe further refined by size selective precipitation. In a preferred embodiment, this may be accomplished by manipulation of solvent composition of the nanocrystallite suspension.

The CdSe nanocrystallites are stabilized in solution by the formation of a lyophilic coating of alkyl groups on the crystallite outer surface. The alkyl groups are provided by the coordinating solvent used during the growth period. The interparticle repulsive force introduced by the lyophilic coating prevents aggregation of the particles in solution. The effectiveness of the stabilization is strongly dependent upon the interaction of the alkyl groups with the solvent. Gradual addition of a non-solvent will lead to the size-dependent flocculation of the nanocrystallites. Non-solvents are those solvents in which the groups which may be associated with the crystallite outer surface show no great affinity. In the present example, where the coordinating group is an alkyl group, suitable non-solvents include low molecular weight alcohols such as methanol, propanol and butanol. This phenomenon may be used to further narrow the particle size distribution of the nanocrystallites by a size-selective precipitation process. Upon sequential addition of a non-solvent, the largest particles are the first to flocculate. The removal of a subset of flocculated particles from the initial solution results in the narrowing of the particle size distribution in both the precipitate and the supernatant.

A wealth of potential organometallic precursors and high boiling point coordinating solvents exist which may used in the preparation of CdSe dots. Organometallic precursors are selected for their stability, ease of preparation and clean decomposition products and low cracking temperatures. A particularly suitable organometallic precursor for use as a Cd source include alkyl cadmium compounds, such as $CdMe_2$. Suitable organometallic precursors for use as a Se source include, bis(trimethylsilyl)selenium (($TMS)_2Se$), (tri-n-octylphosphine)selenide (TOPSe) and trialkyl phosphine selenides, such as (tri-n-butylphosphine)selenide (TBPSe). Other suitable precursors may include both cadmium and selenium in the same molecule. Alkyl phosphines and alkyl phosphine oxide be used as a high boiling coordinating solvent; however, other coordinating solvents, such as pyridines, furans, and amines may also be suitable for the nanocrystallite production.

The preparation of monodisperse CdSe quantum dots has been described in detail in Murray et al. (J. Am. Chem. Soc., 115:8706 (1993)), which is hereby incorporated in its entirety by reference.

Next, the CdSe particles are overcoated by introducing a solution containing zinc and sulfur precursors in a coordinating solvent (e.g., TOP) into a suspension of CdSe nanocrystallites at the desired temperature. The temperature at which the dots are overcoated is related to the quality of the resultant composite particle. Overcoating the CdSe particles at relatively higher temperatures may cause the CdSe seed crystals to begin to grow via Ostwald ripening and deterioration of the size distribution of the particles leading to broader spectral line widths. Overcoating the particles at relatively low temperatures could lead to incomplete decomposition of the precursors or to reduced crystallinity of the ZnS shell. An ideal growth temperature may be determined for each CdSe core size to ensure that the size distribution of the cores remains constant and that shells with a high degree of crystallinity are formed. In preferred embodiments, CdSe crystallites are overcoated using diethyl zinc and hexamethyldisilathiane as the zinc and sulfur precursors. CdSe crystallites having a diameter in the range of about 23 Å–30 Å are overcoated at a temperature in the range of about 135–145° C., and preferably about 140° C. Similarly, nanocrystallites having a diameter of about 35 Å, 40 Å, 48 Å, and 55 Å, respectively, are overcoated at a temperature of about 155–165° C., and preferably about 160° C., 175–185° C. and preferably about 180°C., about 195–205° C., and preferably about 200° C., and about 215–225° C., and about 220° C., respectively. The actual temperature ranges may vary, dependent upon the relative stability of the precursors and the crystallite core and overlayer composition. These temperature ranges may need to be modified 10–20° C., depending upon the relative stability of the precursors. For example, when the more stable trialkyl phosphine chalcogenides (like TOPSe) are used, higher temperatures are employed. The resulting (CdSe)ZnS composite particles are also passivated with TOPO/TOP on their outermost surface.

The ZnS precursor solution concentration and the rate of its addition to the CdSe particles is selected to promote heterogeneous growth of ZnS onto the CdSe nuclei instead of homogeneous nucleation to produce ZnS particles. Conditions favoring heterogeneous growth include dropwise addition, e.g., 1–2 drops/second, of the ZnS precursor solution to the CdSe solution and maintenance of the ZnS precursor solution at low concentrations. Low concentrations typically range from 0.0005–0.5 M. In some preferred embodiments, it may be desirable to include a final purification step in which the overcoated dots are subjected to size selective precipitation to further assure that mainly only (CdSe)ZnS composite particles are present in the final product.

In other embodiments, it may be desirable to modify the crystallite outer surface to permit formation of stable suspensions of the capped quantum dots. The outer surface of the nanocrystal includes an organic layer derived from the coordinating solvent used during the capping layer growth process. The crystallite surface may be modified by repeated exposure to an excess of a competing coordinating group. For example, a dispersion of the capped quantum dot may be treated a coordinating organic compound, such as pyridine, to produce crystallites which dispersed readily in pyridine, methanol, and aromatics but no longer dispersed in aliphatics. Such a surface exchange process may be carried out using a variety of compounds which are capable of coordinating or bonding to the outer surface of the capped quantum dot, such as by way of example, phosphines, thiols, amines and phosphates. In other embodiments, the capped quantum dots may be exposed to short chained polymers which exhibit an affinity for the capped surface on one and which terminate in a moiety having an affinity for the suspension or dispersion medium. Such affinity improves the stability of the suspension and discourages flocculation of the capped quantum dots.

The synthesis described above produces overcoated quantum dots with a range of core and shell sizes. Significantly, the method of the invention allows both the size distribution of the nanocrystallites and the thickness of the overcoating to be independently controlled. FIG. 1 shows the absorption spectra of CdSe dots with a particle size distribution of (a) 23 Å, (b) 42 Å, (c) 48 Å and (d) 55 Å in diameter before (dashed lines) and after (solid lines) overcoating with 1–2 monolayers of ZnS. By "monolayer" as that term is used herein, it is meant a shell of ZnS which measures 3.1 Å (the distance between consecutive planes along the [002] axis in the bulk wurtzite ZnS) along the major axis of the prolate shaped dots. The absorption spectra represents the wavelength and intensity of absorption of light which is absorbed by the quantum dot. FIG. 1 indicates a small shift in the absorption spectra to the red (lower energies) after overcoating due to the partial leakage of the exciton into the ZnS matrix. This red shift is more pronounced in smaller dots where the leakage of the exciton into the ZnS shell has a more dramatic effect on the confinement energies of the charge carriers.

Figure 2:
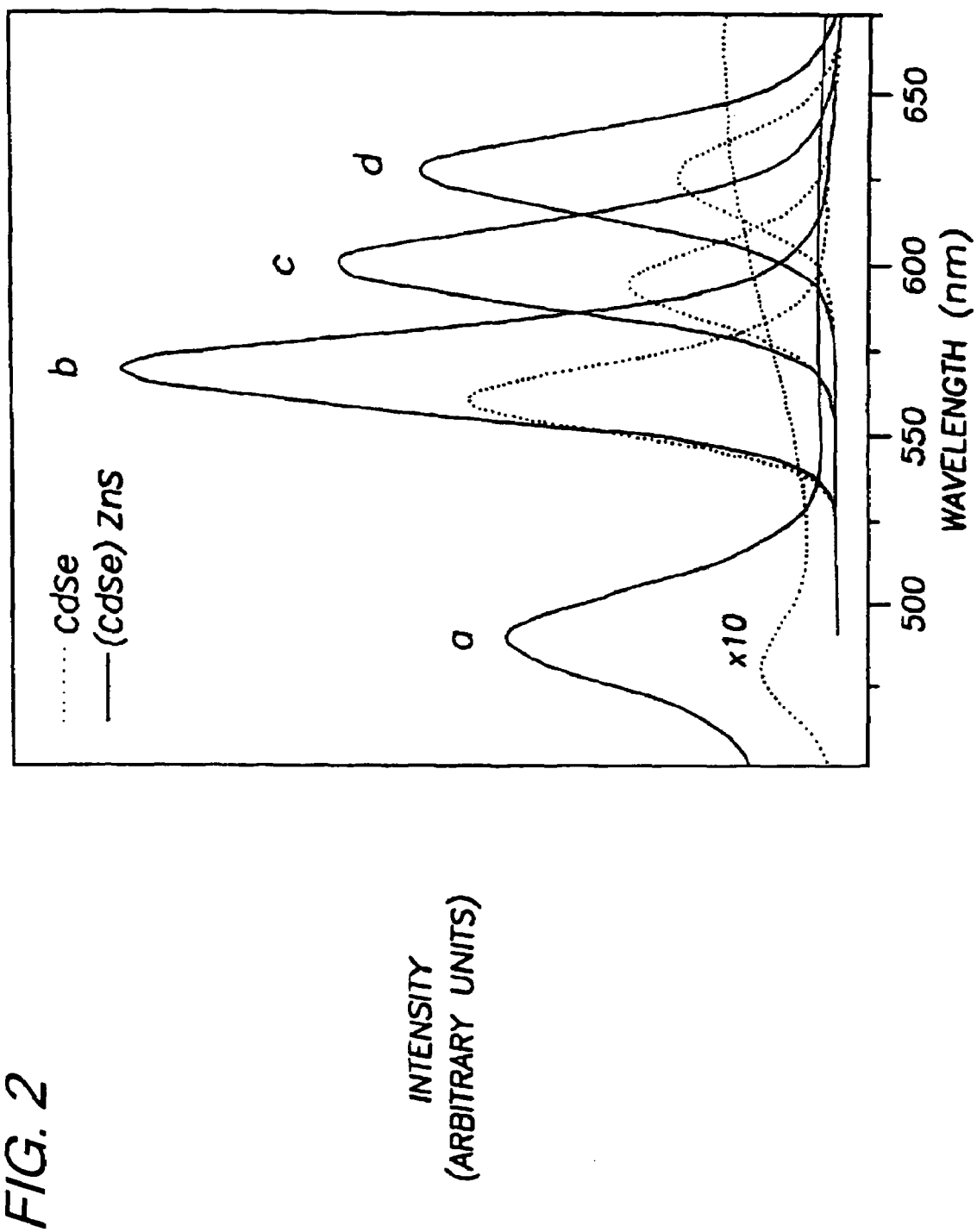
FIG. 2 shows the room temperature photoluminescence (PL) spectra of the samples of FIG. 1 before (dashed lines) and after (solid lines) overcoating with ZnS.

FIG. 2 shows the room temperature photoluminescence spectra (PL) of the samples shown in FIG. 1 before (dashed lines) and after (solid lines) overcoating with ZnS. The PL quantum yield increases from 5–15% for bare dots to values ranging from 30% to 50% for dots passivated with ZnS. The PL spectra are much more intense due to their higher quantum yield of (a) 40%, (b) 50%, (c) 35% and (d) 30%, respectively. The quantum yield reaches a maximum value with the addition of approximately 1.3 monolayers of ZnS. A decrease in quantum yields at higher ZnS coverages may be due to the formation of defects in the ZnS shell.

A color photograph demonstrates the wide spectral range of luminescence from the (CdSe)ZnS composite quantum dots of the present invention. See, for example, FIG. 3 of U.S. Pat. No. 6,207,229, which is incorporated by reference in its entirety. The photograph shows six different samples of ZnS overcoated CdSe dots dispersed in dilute hexane solutions and placed in identical quartz cuvettes. The samples were irradiated with 356 nm ultraviolet light from a uv lamp in order to observe luminescence from all solutions at once. As the size of the CdSe core increased, the color of the luminescence shows a continuous progression from the blue through the green, yellow, orange to red. Their PL peaks occur at (going from right to left in FIG. 3 of U.S. Pat. No. 6,207,229) (a) 470 nm, (b) 480 nm, (c) 520 nm, (d) 560 nm, (e) 594 nm and (f) 620 nm. In contrast, in the smallest sizes of bare TOPO-capped dots, the color of the PL is normally dominated by broad deep trap emissions and appears as faint white light.

Figure 3:
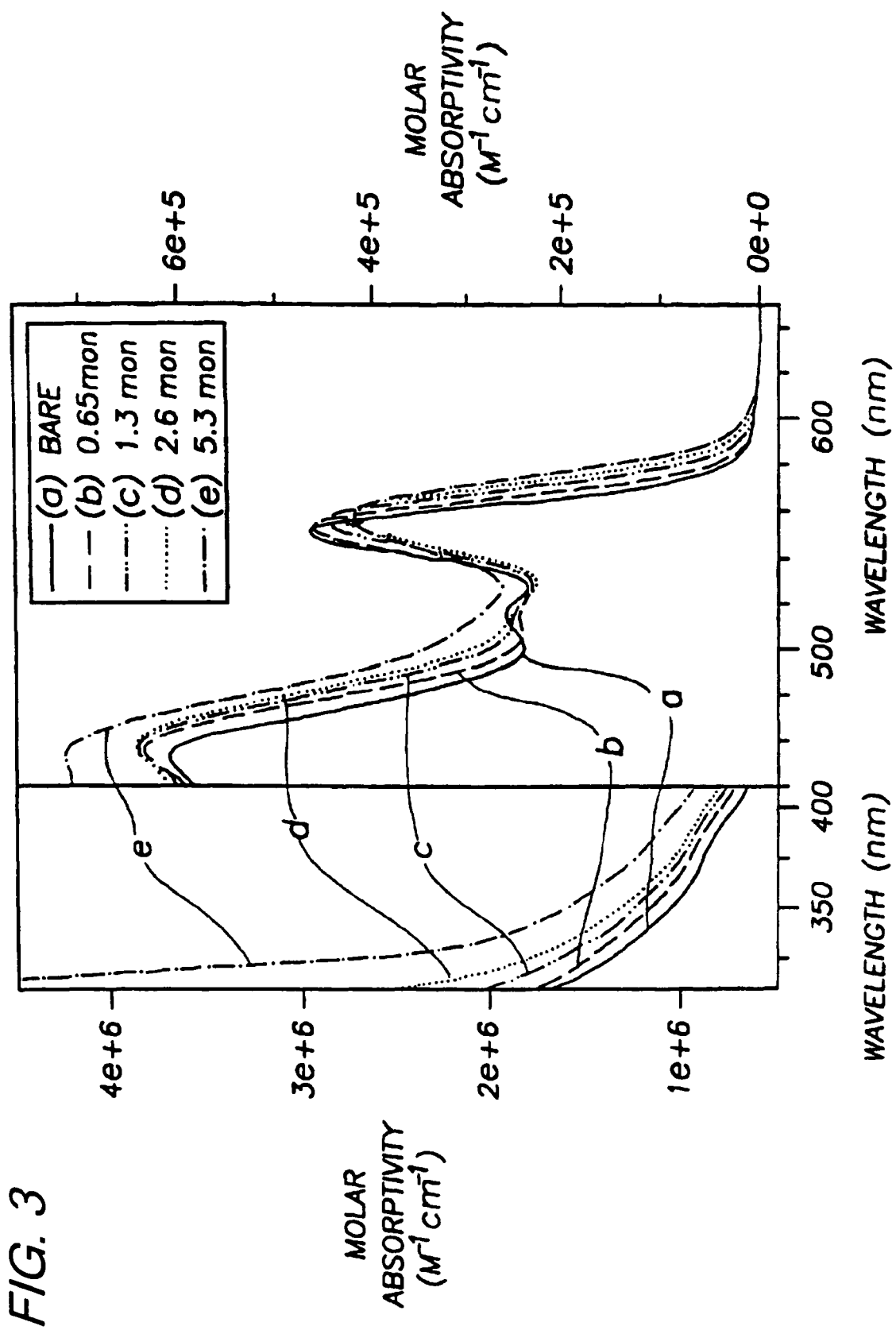
FIG. 3 shows the progression of the absorption spectra for (CdSe)ZnS quantum dots with ZnS coverages of approximately 0, 0.65, 1.3, 2.6 and 5.3 monolayers.

In order to demonstrate the effect of ZnS passivation on the optical and structural properties of CdSe dots, a large quantity of ~40 Å (±10%) diameter CdSe dots were overcoated with varying amounts of Zn and S precursors under identical temperatures and variable times. The result was a series of samples with similar CdSe cores, but with varying ZnS shell thicknesses. FIG. 3 shows the progression of the absorption spectrum for these samples with ZnS coverages of approximately 0 (bare TOPO capped CdSe), 0.65, 1.3, 2.6 and 5.3 monolayers. The right hand side of the figure shows the long wavelength region of the absorption spectra showing the lowest energy optical transitions. The spectra demonstrate an increased red-shift with the thicker ZnS overcoating as well as a broadening of the first peak in the spectra due to increased polydispersity of shell thicknesses. The left hand side of the spectra show the ultra-violet region of the spectra indicating an increased absorption at higher energies with increasing ZnS thickness due to direct absorption into the higher ZnS band gap ZnS shell.

Figure 4:
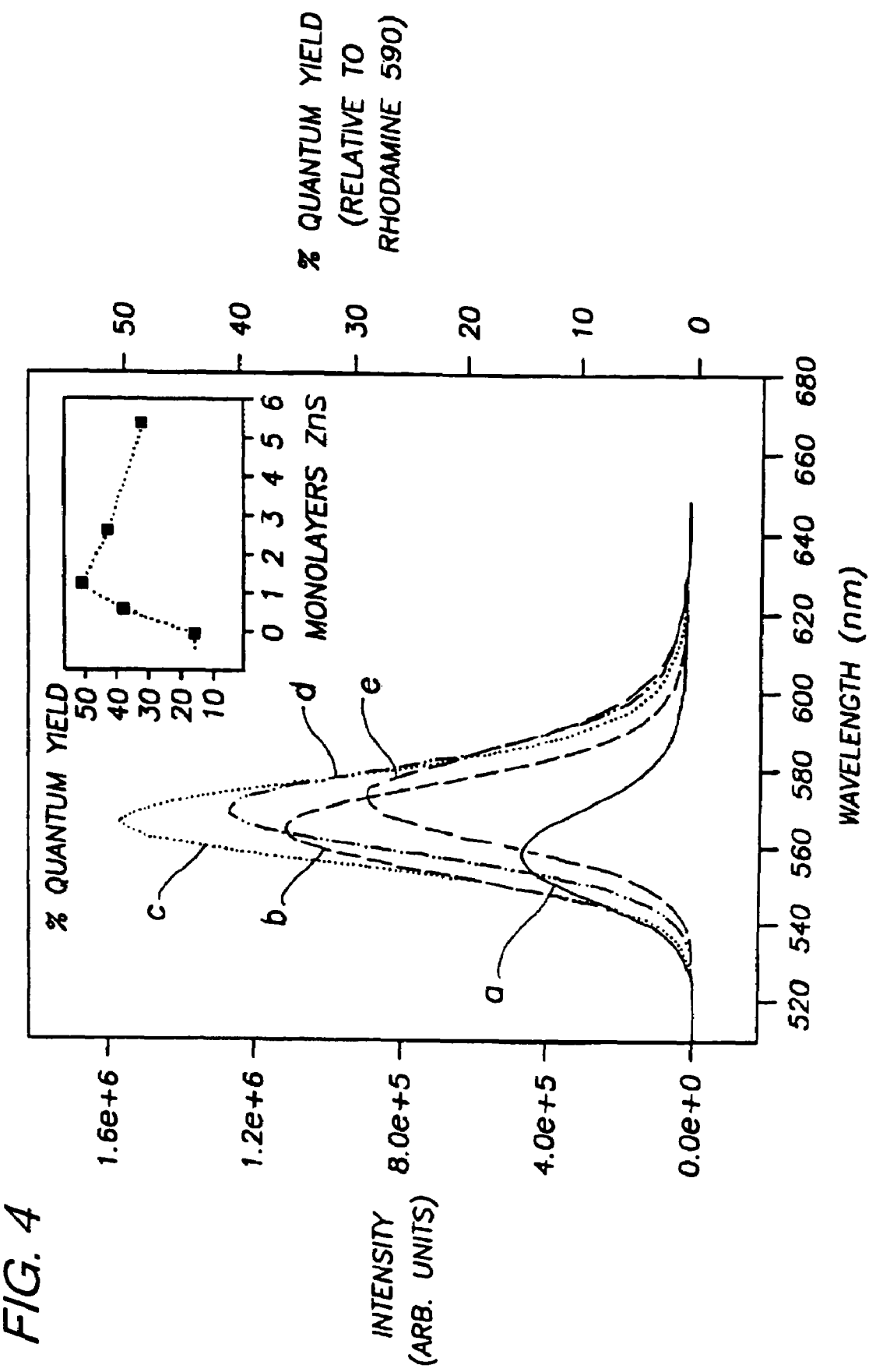
FIG. 4 shows the evolution of the PL for ~40 Å diameter (CdSe)ZnS dots of FIG. 3 with varying ZnS coverage.

The evolution of the PL for the same ~40 Å diameter CdSe dots with ZnS coverage is displayed in FIG. 4. As the coverage of ZnS on the CdSe surface increases one observes a dramatic increase in the fluorescence quantum yield followed by a steady decline after ~1.3 monolayers of ZnS. The spectra are red shifted (slightly more than the shift in the absorption spectra) and show an increased broadening at higher coverages. The inset to FIG. 4 charts the evolution of the quantum yield for these dots as a function of the ZnS shell thickness. For this particular sample, the quantum yield started at 15% for the bare TOPO capped CdSe dots and increased with the addition of ZnS approaching a maximum value of 50% at approximately ~1.3 monolayer coverage. At higher coverages, the quantum yield began to decrease steadily until it reached a value of about 30% at about 5 monolayers coverage.

Although the invention has been described with reference to the preparation and performance of CdSe(ZnS), it will be readily apparent that the method of preparation may be used to obtain monodisperse overcoated quantum dots with various combinations of nanocrystallite core and overcoating. The method of the invention permits the preparation of a variety of capped nanocrystals having a very narrow particle size distribution and exhibiting improvements in color purity and intensity of their photoluminescent emissions. It is contemplated that a variety of cadmium chalcogenides, for example, CdX, where X=S, Se, Te may be prepared and overcoated according to the method of the invention. It is further contemplated that the overcoating may be varied and may include, by way of example only, ZnS, ZnSe, CdS and mixtures thereof.

The invention is described with reference to the following examples, which are presented for the purpose of illustration and which are not intended to be limiting of the invention, the scope of which is set forth in the claims which follow this specification.

EXAMPLE 1

Preparation of CdSe. Trioctylphosphine oxide (TOPO, 90% pure) and trioctylphosphine (TOP, 95% pure) were obtained from Strem and Fluka, respectively. Dimethyl cadmium ($CdMe_2$) and diethyl zinc ($ZnEt_2$) were purchased from Alfa and Fluka, respectively, and both materials were filtered separately through a 0.2 μm filter in an inert atmosphere box. Trioctylphosphine selenide was prepare by dissolving 0.1 mols of Se shot in 100 ml of TOP thus producing a 1 M solution of TOPSe. Hexamethyl(disilathiane) ($TMS_2 S$) was used as purchased from Aldrich. HPLC grade n-hexane, methanol, pyridine and n-butanol were purchased from EM Sciences.

The typical preparation of TOP/TOPO capped CdSe nanocrystallites follows. TOPO (30 g) was placed in a flask and dried under vacuum (~1 Torr) at 180° C. for 1 hour. The flask was then filled with nitrogen and heated to 350° C. In an inert atmosphere drybox the following injection solution was prepared: $CdMe_2$ (200 microliters, 2.78 mol), 1 M TOPSe solution (4.0 mL, 4.0 mmol), and TOP (16 mL). The injection solution was thoroughly mixed, loaded into a syringe, and removed from the drybox.

The heat was removed from the reaction flask and the reagent mixture was delivered into the vigorously stirring TOPO with a single continuous injection. This produces a deep yellow/orange solution with a sharp absorption feature at 470–500 nm and a sudden temperature decrease to ~240° C. Heating was restored to the reaction flask and the temperature was gradually raised to 260–280° C.

Aliquots of the reaction solution were removed at regular intervals (5–10 min) and absorption spectra taken to monitor the growth of the crystallites. The best samples were prepared over a period of a few hours steady growth by modulating the growth temperature in response to changes in the size distribution, as estimated from the sharpness of the features in the absorption spectra. The temperature was lowered 5–10° C. in response to an increase in the size distribution. Alternatively, the reaction can also be stopped at this point. When growth appears to stop, the temperature is raised 5–10° C. When the desired absorption characteristics were observed, the reaction flask was allowed to cool to ~60° C. and 20 mL of butanol were added to prevent solidification of the TOPO. Addition of a large excess of methanol causes the particles to flocculate. The flocculate was separated from the supernatant liquid by centrifugation; the resulting powder can be dispersed in a variety of organic solvents (alkanes, ethers, chloroform, tetrahydrofuran, toluene, etc.) to produce an optically clear solution.

Size-selective Precipitation. Nanocrystallites were dispersed in a solution of ~10% butanol in hexane. Methanol was then added dropwise to this stirring solution until opalescence persisted. Separation of supernatant and flocculate by centrifugation produced a precipitate enriched with the largest crystallites in the sample. This procedure was repeated until no further sharpening of the optical absorption spectrum was noted. Size-selective precipitation can be carried out in a variety of solvent/nonsolvent pairs, including pyridine/hexane and chloroform/methanol.

Surface Exchange. Crystallite surface derivatization can be modified by repeated exposure to an excess of a competing capping group. Heating to ~60° C. a mixture of ~50 mg of TOPO/TOP capped crystallites and 5–10 mL of pyridine gradually dispersed the crystallites in the solvent. Treatment of the dispersion with excess hexane resulted in the flocculation of the crystallites which are then isolated by centrifugation. The process of dispersion in pyridine and flocculation with hexane was repeated a number of times to produce crystallites which dispersed readily in pyridine, methanol, and aromatics but no longer dispersed in aliphatics.

EXAMPLE 2

Preparation of CdSe. A second route to the production of CdSe core replaces the phosphine chalcogenide precursors in Example 1 with $(TMS)_2Se$. The smallest (~12 Å) CdSe species are produced under milder conditions with injection and growth carried out at ~100° C. The product was further treated as described in Example 1.

EXAMPLE 3

Preparation of (CdSe)ZnS. Nearly monodisperse CdSe quantum dots ranging from 23 Å to 55 Å in diameter were synthesized and purified via size-selective precipitation as described in Example 1.

A flask containing 5 g of TOPO was heated to 190° C. under vacuum for several hours then cooled to 60° C. after which 0.5 mL trioctylphosphine (TOP) was added.

Roughly 0.1–0.4 μmols of CdSe dots dispersed in hexane were transferred into the reaction vessel via syringe and the solvent was pumped off.

Diethyl zinc ($ZnEt_2$) and hexamethyldisilathiane ($(TMS)_2 S$) were used as the Zn and S precursors, respectively. The amounts of Zn and S precursors needed to grow a ZnS shell of desired thickness for each CdSe sample were determined as follows: First, the average radius of the CdSe dots was estimated from TEM or SAXS measurements. Next, the ratio of ZnS to CdSe necessary to form a shell of desired thickness was calculated based on the ratio of the shell volume to that of the core assuming a spherical core and shell and taking into account the bulk lattice parameters of CdSe and ZnS. For larger particles the ratio of Zn to Cd necessary to achieve the same thickness shell is less than for the smaller dots. The actual amount of ZnS that grows onto the CdSe cores was generally less than the amount added due to incomplete reaction of the precursors and to loss of some material on the walls of the flask during the addition.

Equimolar amounts of the precursors were dissolved in 2–4 mL TOP inside an inert atmosphere glove box. The precursor solution was loaded into a syringe and transferred to an addition finnel attached to the reaction flask. The reaction flask containing CdSe dots dispersed in TOPO and TOP was heated under an atmosphere of $N_2$. The temperature at which the precursors were added ranged from 140° C. for 23 Å diameter dots to 220° C. for 55 Å diameter dots. When the desired temperature was reached the Zn and S precursors were added dropwise to the vigorously stirring reaction mixture over a period of 5–10 minutes.

After the addition was complete the mixture was cooled to 90° C. and left stirring for several hours. Butanol (5 mL) was added to the mixture to prevent the TOPO from solidifying upon cooling to room temperature. The overcoated particles were stored in their growth solution to ensure that the surface of the dots remained passivated with TOPO. They were later recovered in powder form by precipitating with methanol and redispersing into a variety of solvents including hexane, chloroform, toluene, THF and pyridine.

In some cases, the as-grown CdSe crystallites were judged to be sufficiently monodisperse that no size-selective precipitation was performed. Once these CdSe particles had grown to the desired size, the temperature of the reaction flask was lowered and the Zn and S precursors were added dropwise to form the overcapping.

Optical Characterization. UV-Visible absorption spectra were acquired on an HP 8452 diode array spectrophotometer. Dilute solutions of dots in hexane were placed in 1 cm quartz cuvettes and their absorption and corresponding florescence were measured. The photoluminescence spectra were taken on a SPEX Fluorolog-2 spectrometer in front face collection mode. The room temperature quantum yields were determined by comparing the integrated emission of the dots in solution to the emission of a solution of rhodamine 590 or rhodamine 640 of identical optical density at the excitation wavelength.

What is claimed is:

1. A population of coated nanocrystals each comprising a size-selected core including a first semiconductor material and an overcoating including a second semiconductor material, wherein the population of coated nanocrystals exhibit photoluminescence having a quantum yield of greater than about 30%.

2. The population of coated nanocrystals of claim 1, wherein the population of coated nanocrystals exhibit photoluminescence having a quantum yield of between about 30% and 50%.

3. The population of coated nanocrystals of claim 1, wherein the population of coated nanocrystals exhibit photoluminescence having a quantum yield of greater than about 40%.

4. The population of coated nanocrystals of claim 1, wherein the population of coated nanocrystals exhibit photoluminescence having a quantum yield of about 50%.

5. The population of coated nanocrystals of claim 1, wherein the size-selected cores of the population of coated nanocrystals have diameters having no greater than 10% rms deviation.

6. The population of coated nanocrystals of claim 1, wherein the size-selected cores of the population of coated nanocrystals have diameters having no greater than 5% rms deviation.

7. The population of coated nanocrystals of claim 1, wherein the second semiconductor material is ZnS.

8. The population of coated nanocrystals of claim 7, wherein the overcoating of ZnS includes one to two monolayers of ZnS.

9. The population of coated nanocrystals of claim 7, wherein the overcoating of ZnS includes about 1.3 monolayers of ZnS.

10. The population of coated nanocrystals of claim 7, wherein the overcoating of ZnS includes more than two monolayers of ZnS.

11. The population of coated nanocrystals of claim 1, further comprising one or more organic layers on the outer surface of the population of coated nanocrystals.

12. The population of coated nanocrystals of claim 1, wherein the population of coated nanocrystals emit light in a spectral range of no greater than about 60 nm full width at half max (FWHM) when irradiated.

13. The population of coated nanocrystals of claim 7, wherein the first semiconductor material is selected from CdS, CdSe, CdTe, and mixtures thereof.

14. The population of coated nanocrystals of claim 1, wherein the population of coated nanocrystals emit light in a spectral range of no greater than about 0.05 eV full width at half max (FWHM) when irradiated.

15. The population of coated nanocrystals of claim 1, wherein the population of coated nanocrystals emit light in a spectral range of no greater than about 0.03 eV full width at half max (FWHM) when irradiated.

16. A population of coated nanocrystals comprising a core including a first semiconductor material and an overcoating of ZnS, wherein the cores of the population of nanocrystals have diameters having no greater than 10% rms deviation.

17. The population of coated nanocrystals of claim 16, wherein the population of coated nanocrystals exhibit photoluminescence having a quantum yield of between about 30% and 50%.

18. The population of coated nanocrystals of claim 16, wherein the population of coated nanocrystals exhibit photoluminescence having a quantum yield of greater than about 40%.

19. The population of coated nanocrystals of claim 16, wherein the population of coated nanocrystals exhibit photoluminescence having a quantum yield of about 50%.

20. The population of coated nanocrystals of claim 16, wherein the population of coated nanocrystals emit light in a spectral range of no greater than about 0.05 eV full width at half max (FWHM) when irradiated.

21. The population of coated nanocrystals of claim 16, wherein the population of coated nanocrystals emit light in a spectral range of no greater than about 0.03 eV full width at half max (FWHM) when irradiated.

22. The population of coated nanocrystals of claim 16, wherein the overcoating of ZnS includes one to two monolayers of ZnS.

23. The population of coated nanocrystals of claim 16, wherein the overcoating of ZnS includes about 1.3 monolayers of ZnS.

24. The population of coated nanocrystals of claim 16, wherein the overcoating of ZnS includes more than two monolayers of ZnS.

25. The population of coated nanocrystals of claim 16, further comprising one or more organic layers on the outer surface of the coated nanocrystals.

26. A population of coated nanocrystals comprising a size-selected core including a first semiconductor material selected from CdS, CdSe, CdTe and an overcoating of ZnS.

27. A population of coated nanocrystals comprising a core including a first semiconductor material and an overcoating of ZnS, wherein the population of coated nanocrystals emit light in a spectral range of no greater than about 0.05 eV at full width half max (FWHM) when irradiated.

28. The population of coated nanocrystals of claim 27, wherein the population of coated nanocrystals emit light in a spectral range of no greater than about 0.03 eV at full width half max (FWHM) when irradiated.

29. The population of coated nanocrystals of claim 27, wherein the cores are size-selected by size-selective precipitation.

30. The population of coated nanocrystals of claim 27, wherein the population of coated nanocrystals exhibit photoluminescence having a quantum yield of greater than about 30%.

* * * * *

(12) INTER PARTES REEXAMINATION CERTIFICATE (694th)
United States Patent
Bawendi et al.

(10) Number: US 7,125,605 C1
(45) Certificate Issued: Sep. 18, 2013

(54) HIGHLY LUMINESCENT COLOR-SELECTIVE NANOCRYSTALLINE MATERIALS

(75) Inventors: Moungi Bawendi, Boston, MA (US); Klavs F. Jensen, Lexington, MA (US); Bashir O. Dabbousi, Dhahran (SA); Javier Rodriguez-Viejo, Sant Cugat del Valles (ES); Frederic Victor Mikulec, Somerville, MA (US)

(73) Assignee: National Science Foundation, Arlington, VA (US)

Reexamination Request:
No. 95/001,298, Feb. 26, 2010

Reexamination Certificate for:
Patent No.: 7,125,605
Issued: Oct. 24, 2006
Appl. No.: 10/960,947
Filed: Oct. 12, 2004

Related U.S. Application Data

(63) Continuation of application No. 10/642,578, filed on Aug. 19, 2003, now Pat. No. 6,861,155, which is a continuation of application No. 09/625,861, filed on Jul. 26, 2000, now Pat. No. 6,607,829, and a continuation-in-part of application No. 08/969,302, filed on Nov. 13, 1997, now Pat. No. 6,322,901.

(60) Provisional application No. 60/145,708, filed on Jul. 26, 1999.

(51) Int. Cl.
| | |
|---|---|
| *B23B 5/16* | (2006.01) |
| *C01B 19/00* | (2006.01) |
| *C07F 9/22* | (2006.01) |
| *C07F 9/53* | (2006.01) |
| *C30B 7/00* | (2006.01) |
| *H01L 33/00* | (2010.01) |

(52) U.S. Cl.
USPC ............ 428/403; 257/E33.004; 257/E33.005; 977/813; 977/832

(58) Field of Classification Search
None
See application file for complete search history.

(56) References Cited

To view the complete listing of prior art documents cited during the proceeding for Reexamination Control Number 95/001,298, please refer to the USPTO's public Patent Application Information Retrieval (PAIR) system under the Display References tab.

*Primary Examiner* — Alan Diamond

(57) ABSTRACT

A nanocrystal capable of light emission includes a nanoparticle having photoluminescence having quantum yields of greater than 30%.

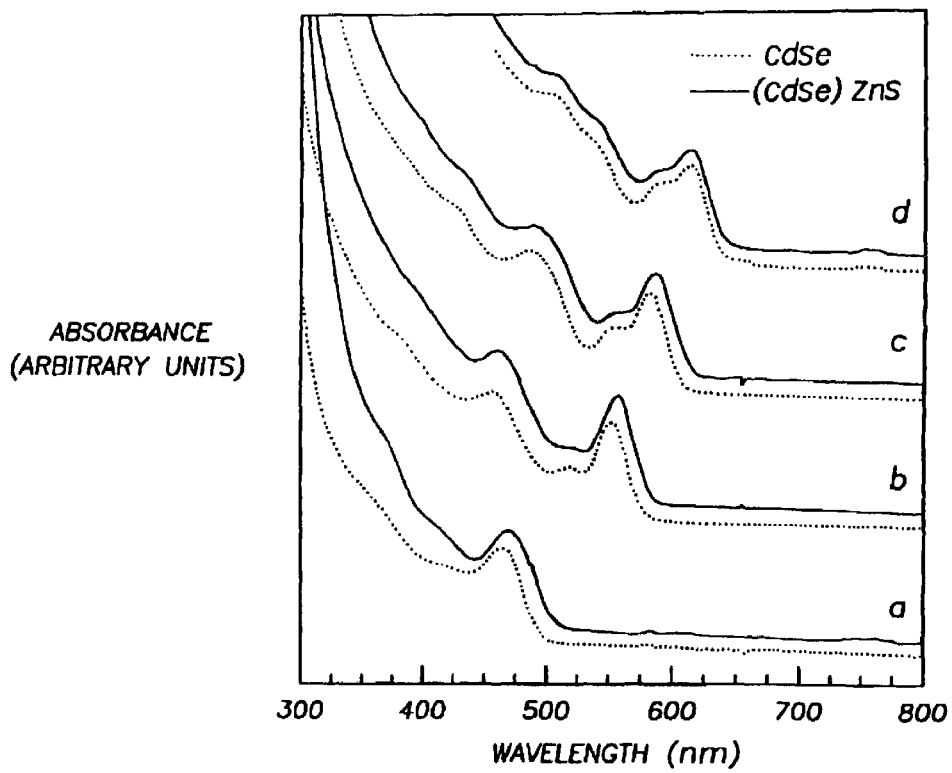

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-30 are cancelled.

\* \* \* \* \*